(12) United States Patent
van de Goor et al.

(10) Patent No.: US 6,859,050 B2
(45) Date of Patent: Feb. 22, 2005

(54) HIGH FREQUENCY CONTACTLESS HEATING WITH TEMPERATURE AND/OR CONDUCTIVITY MONITORING

(75) Inventors: Tom A van de Goor, San Mateo, CA (US); Klaus E Witt, Koltern (DE); Bohuslav Gas, Jilove u Prahy (CZ); Jiri Zuska, Praha (CZ)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/159,519

(22) Filed: May 31, 2002

(65) Prior Publication Data

US 2003/0222664 A1 Dec. 4, 2003

(51) Int. Cl.[7] .......................... G01R 27/08; H05B 6/62
(52) U.S. Cl. ...................... 324/695; 324/693; 219/772
(58) Field of Search ................ 219/772, 779, 219/667; 324/693, 691, 686, 441, 719, 721

(56) References Cited

U.S. PATENT DOCUMENTS

| | | |
|---|---|---|
| 3,944,917 A | 3/1976 | Hogg, Walter R. et al. |
| 4,683,195 A | 7/1987 | Mullis et al. |
| 4,972,137 A | 11/1990 | Dunstan et al. |
| 5,269,901 A | 12/1993 | Dill et al. |
| 5,270,183 A | 12/1993 | Corbett et al. |
| 5,341,100 A | 8/1994 | Taylor |
| 5,385,654 A | 1/1995 | Kelly et al. |
| 5,498,392 A | 3/1996 | Wilding et al. |
| 5,646,039 A | 7/1997 | Northrup et al. |
| 5,656,493 A | 8/1997 | Mullis et al. |
| 5,658,413 A | 8/1997 | Kaltenbach et al. |
| 5,965,410 A | 10/1999 | Chow et al. |
| 6,132,580 A | 10/2000 | Mathies et al. |
| 6,174,675 B1 | 1/2001 | Chow et al. |
| 6,210,882 B1 | 4/2001 | Landers et al. |
| 6,350,973 B2 | 2/2002 | Wroe et al. |
| 6,386,050 B1 | 5/2002 | Yin et al. |
| 6,638,605 B1 | 5/2002 | Yin et al. |
| 6,441,625 B1 | 8/2002 | McAllister et al. |
| 6,489,785 B2 | 12/2002 | McAllister |
| 2001/0007769 A1 | 7/2001 | Wittwer et al. |
| 2002/0092363 A1 * | 7/2002 | Jorgenson et al. ....... 73/861.95 |

FOREIGN PATENT DOCUMENTS

| | | |
|---|---|---|
| WO | WO00/09851 | 8/1999 |
| WO | WO02/11886 A2 | 8/2001 |

OTHER PUBLICATIONS

D. Kaniansky; V. Zelenske; M. Masar; F. Ivanyi; S. Gazdikova, "Contactless conductivity detection in capillary zone electrophoresis"; Journal of Chromatography A, 844 (199), pp. 349–359, Date: Mar. 1999.

Jiri Vacik; Jiri Zuska and Iva Musalasova, "Improvement of the Performance of a High–Frequency Contactless Conductivity Detector for Isotachophoresis", Chrom. 17, 322; pp. 234–240, Date: 1985.

B. Gas; M. Demjsnenko; and J. Vacik, "High–Frequency Contctless Conductivity Detection in Isotachophoresis", Journal of Chromatography, 192 (1980), pp. 253–257.

Jose A. Fracssi de Silva and Claudimir I. do Lago; "An Oscillometric Detector for Capillary Electrophoresis", Analytical Chemistry, vol. 70, No. 20, Oct. 15, 1998; pp. 43339–44343.

Andreas J. Zemann; Erhard Schnell, Dietmnar Volggar and Gunther K. Bonn; "Contactless Conductivity Detection for Capitally Electrophoresis", Analytical Chemistry, vol. 70, No. 3, Feb. 1, 1998; pp. 563–567.

* cited by examiner

*Primary Examiner*—Anjan Deb
*Assistant Examiner*—Amy He
(74) *Attorney, Agent, or Firm*—Michael J. Beck (57) ABSTRACT

Devices and methods for contactless heating of a fluid in a chamber using a high frequency alternating potential are described. At least two electrodes are coupled to the chamber such that the alternating potential is coupled to the fluid inside the chamber and heats the fluid. A control loop derives a signal from the alternating potential and uses the signal to control the alternating potential. The devices and methods described determine temperature and/or conductivity of the fluid using the signal.

27 Claims, 6 Drawing Sheets

HIGH FREQUENCY CONTACTLESS HEATING WITH TEMPERATURE AND/OR CONDUCTIVITY MONITORING

DESCRIPTION

1. Field of the Invention

The invention relates generally to analytical chemistry and biochemistry. More specifically, the invention relates to heating of a fluid and measuring the temperature and/or conductivity of the fluid.

2. Background of the Invention

The field of analytical chemistry and biochemistry is concerned with the measurement of properties of substances, such as solutions of chemicals, biochemicals, or other analytes. Increasingly useful and powerful methods and apparatus have enabled detection or identification of analytes in increasingly smaller amounts or under more useful conditions. In particular, analysis methods based on chemical reactions often require at least monitoring, if not controlling temperature to a certain level. Thermostating during analysis is known to be an important factor in capillary electrophoresis (CE) applications, as can be seen in U.S. Pat. No. 5,269,901 to Dill et al. (1993) and U.S. Pat. No. 5,385,654 to Kelly et al. (1995). An important method frequently used in analysis of DNA is the polymerase chain reaction (PCR), and a host of methods related to PCR have been developed. The principle of nucleic acid amplification is described in U.S. Pat. No. 4,683,195 to Mullis et al. (1987). Such methods typically involve controlling the temperature of a reactant solution through a number of temperature cycles. The reactant solution will usually contain nucleotide monomers, enzymes, oligonucleotide primers, and polynucleotides. A suitable reactant solution, when put through a number of heating and cooling cycles, will result in amplification of certain polynucleotides. A small amount of polynucleotide can thus lead to a large amount of polynucleotide, which is then easier to detect. The temperature cycling is an important aspect of the process and a number of devices used for temperature cycling of reactant solutions are known. See U.S. Pat. No. 4,683,195 to Mullis et al. (1987); U.S. Pat. No. 5,498,392 to Wilding et al. (1996); U.S. Pat. No. 5,270,183 to Corbett et al. (1993); and U.S. Pat. No. 5,656,493 to Mullis et al. (1997). See also international application WO 00/09651 to Wittwer et al. (2000) which describes a thermal cycler using electrodes in contact with the sample to provide resistive heating. Such devices need to provide for controlled heating of the reactant solution to maintain the reactant solution at designated temperatures for designated amounts of time each cycle.

Analysis of sample fluid may be enhanced if the sample fluid is put through a separation process (for example, chromatography or electrophoresis) prior to analysis to separate components in the sample fluid. Analytical instruments may then be used to measure certain parameters, such as conductivity, fluorescence, or ultra-violet (UV) absorption, of the separated components by passing the separated components through a detection region in the analytical instrument. Conductivity detection is useful for detecting components with measurable conductivity. Fluorescence detection and UV absorption detection both are useful for detecting components with measurable response to incident light.

Conductivity detection can be implemented by locating electrodes on the interior walls of the detection region of the analytical instrument, in direct contact with the sample fluid. Typically, the detection region includes a fluid flow channel and "transmit" (or "drive") and "receive" (or "detection") electrodes. The channel holds the sample fluid (containing the component to be analyzed), and the "transmit" (or "drive") and "receive" (or "detection") electrodes oppose each other across a transverse width or diameter of the fluid flow channel. However, since the electrodes are in contact with the sample fluid, electrochemical reactions at the electrodes can affect both the electrodes and the sample fluid. Such interaction can cause undesirable artifacts within a run and undermines repeatability between runs. This undesirable interaction between sample and electrodes is avoided by "contactless" conductivity detection.

Contactless conductivity detection is taught by Gas B., Demjanenko M., Vacik J., "High-Frequency Contactless Conductivity Detection In Isotachophoresis", J. Chromatog. (1980) 192:253–257; Jose A. Fracassi da Silva & Claudimir L. do Lago, "An Oscillometric Detector for Capillary Electrophoresis", Anal. Chem. (1998) 70:4339–4343; Jiri Vacik, Jiri Zuska & Iva Muselasova, "Improvement of the Performance of a High-Frequency Conductivity Detector for Isotachophoresis", J. Chromatog. (1985) 17:322–27; Andress J. Zemann, Erhard Schnell, Dietmar Volger, & Guinther K. Bonn, "Contactless Conductivity Detection for Capillary Electrophoresis", Anal. Chem. (1998) 70:563–567. See also U.S. Pat. No. 5,658,413 to Kaltenbach et al. (1997) "Miniaturized planar columns in novel support media for liquid phase analysis." In addition, an antisynchronously driven contactless conductivity detector is the subject of commonly owned U.S. patent application Ser. No. 09/576,690 filed May 23, 2000, entitled "Sample-Analysis System with Antisynchronously Driven Contactless Conductivity Detection" by Gary B. Gordon and Tom A. van de Goor. Commonly owned U.S. patent application Ser. No. 09/626,521 filed Jul. 26, 2001, entitled "Contactless Conductivity Detector With Transmitter/Receiver Electrode" by McAllister et al. provides a contactless conductivity detector in which a "signal" electrode is used to both drive the excitation signal and sense the response in a contactless conductivity detector. Commonly owned U.S. patent application Ser. No. 09/730,645 filed Dec. 5, 2000, entitled "Comparative Contactless Conductivity Detector" by McAllister provides a comparative contactless-conductivity detection system with two channel assemblies, each with a fluid channel, antisynchronously driven drive electrodes, and detection electrodes. All patents and other publications cited herein are hereby incorporated by reference in their entirety.

In contactless conductivity detection, electrodes are often capacitively coupled to the sample fluid through a channel wall. To this end, the electrodes can be formed on the exterior surface of the channel wall. Since the electrodes are not in contact with sample fluid, artifacts due to chemical interactions at the electrodes are eliminated and reproducibility is improved.

Fluorescence detection and UV absorption detection, although being useful detection alternatives to conductivity detection, both require the inclusion of related optics in the analytical instrument, which can add to the complexity and cost of the analytical instrument.

Heating of a sample fluid in an analytical instrument has been accomplished in numerous ways, including direct contact heating (continuous-flow PCR on chip, see Science (1998) 280:1046-ff] or "Apparatus for Diagnostic Assays" WO 02/11886 A2 to Molecular Sensing (Feb. 14, 2002) ), infra-red radiative heating ("Infrared-Mediated Thermocycling for Ultrafast Polymerase Chain Reaction Amplification of DNA", R. P. Oda, M. A. Strausbauch, et al., Anal. Chem.

(1998) 70:4361–68), or resistive heating. See U.S. Pat. No. 5,965,410 to Chow et al. (1999); U.S. Pat. No. 6,174,675 to Chow (Jan. 16, 2001); U.S. Pat. No. 6,210,882 to Landers et al. (Apr. 3, 2001); U.S. Pat. No. 6,132,580 to Mathies et al. (2000); U.S. Pat. No. 5,646,039 to Northrup et al. (1997). Especially critical and fast chemical reactions require a homogenous distribution of temperature across the reaction volume (see Proc. Nat. Acad. Sci. (1996) 93:5556-ff).

Temperature measurement of the sample fluid may be accomplished by, e.g. measuring the temperature of the structure surrounding the fluid (such as the walls of a fluid flow channel), inserting a temperature sensor directly into the fluid, or by measuring the temperature of a reference fluid. See R. P. Oda, M. A. Strausbauch, et al., Anal. Chem. (1998) 70:4361–68. However, any method of heating or of temperature measurement that creates a contact with the fluid runs the risk of contamination of the sample fluid (see Adam T. Woolley et al., "Functional Integration of PCR Amplification and Capillary Electrophoresis in a Microfabricated DNA Analysis Device", Anal.Chem. (1996) 68:4081–86. Analytical processes, especially chemical reactions, can be affected by, e.g. the presence of metals or other materials that may leach from a temperature sensor or heating element in direct contact with the sample fluid, thereby contaminating the sample fluid. Therefore, a contactless method, such as measuring temperature of the structure surrounding the fluid, may be a preferred method. However, when measuring the temperature of the structure surrounding the fluid, errors may be introduced into the measurement due to thermal conductance and thermal capacity of the structure or presence of a temperature gradient in the fluid or the surrounding structure.

Moreover, in an instrument performing several functions (separation, detection, heating, temperature measurement) separate circuitry and other components may be necessary for each of the functions. As instruments become smaller and deal with smaller amounts of sample fluid, it may become difficult or expensive to design the instrument (see Jing Cheng et al., "Degenerate Oligonucleotide Primed-Polymerase Chain Reaction and Capillary Electrophoretic Analysis of Human DNA on Microchip-Based Devices", Anal. Biochem. (1998) 257:101-ff; "Apparatus for Diagnostic Assays" WO 02/11886 A2 to Molecular Sensing (Feb. 14, 2002); see also www.molecular-sensiny.com). Interferences within the instrument become a significant factor to consider in designing the instrument, and decoupling of integrated functionality (reducing or designing around interference between elements of the instrument) is a strong consideration.

What is needed is a way of performing multiple functions, e.g. heating and temperature measurement, on a sample fluid that prevents contamination of the sample fluid and provides for simplifying the design of the instrument.

SUMMARY OF THE INVENTION

The invention is thus addressed to the aforementioned deficiencies in the art, and provides novel methods and apparatus for controlled heating of a sample fluid in a chamber through high frequency heating. At least two electrodes are coupled to the chamber such that a high frequency alternating potential applied to at least one of the electrodes is coupled to the fluid inside the chamber and heats the fluid. The electrodes are separated from the fluid by an insulative material and thus do not physically contact the fluid. A control loop derives a modified signal from the applied alternating high frequency potential that is dependent on at least one characteristic of the fluid. The modified signal is used to control the high frequency alternating potential. The apparatus and methods described include means of determining temperature and/or conductivity of the fluid using the modified signal.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein.

To facilitate understanding, identical reference numerals have been used, where practical, to designate corresponding elements that are common to the Figures. Figure components are not drawn to scale.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. In this specification and in the claims that follow, reference will be made to a number of terms that shall be defined to have the following meanings unless a contrary intention is apparent:

"Contactless electrode" herein means that the electrode does not come into physical contact with the workpiece (e.g. the fluid in the chamber) that is the recipient of some signal from the electrode, so there is no direct electrical or chemical contact of the fluid by the electrode. "Contactless measurement" refers to measurement of a property of an analyte by a method which doesn't involve physically contacting the analyte with the sensor. "Contactless heating" refers to a method of heating a substance such as a fluid without physical contact of the substance by the component used to heat the substance. "Contactless coupling" refers to a coupling between an electrode and a fluid without physical contact of the fluid by the electrode, as in where there is an insulative material separating the electrode from the fluid; such coupling may be, e.g. via capacitive coupling, inductive coupling, or electromagnetic coupling. A material having a "chemical insulative property" is inert to the fluid or reaction solution that the material is in contact with. Viewed another way, a fluid or reaction solution that comes into contact with a chemically inert material (one that is chemically insulative) is not chemically altered by that material. A material having an "electrical insulative property" has a high resistance to the flow of direct electric current (d-c) through the material (has a low d-c conductance).

In order to better appreciate how the above described invention is practiced, a more particular description will now be rendered with reference to the appended Figures. The following description is of typical embodiments of the invention and is not to be considered limiting in scope.

Figure 1A:
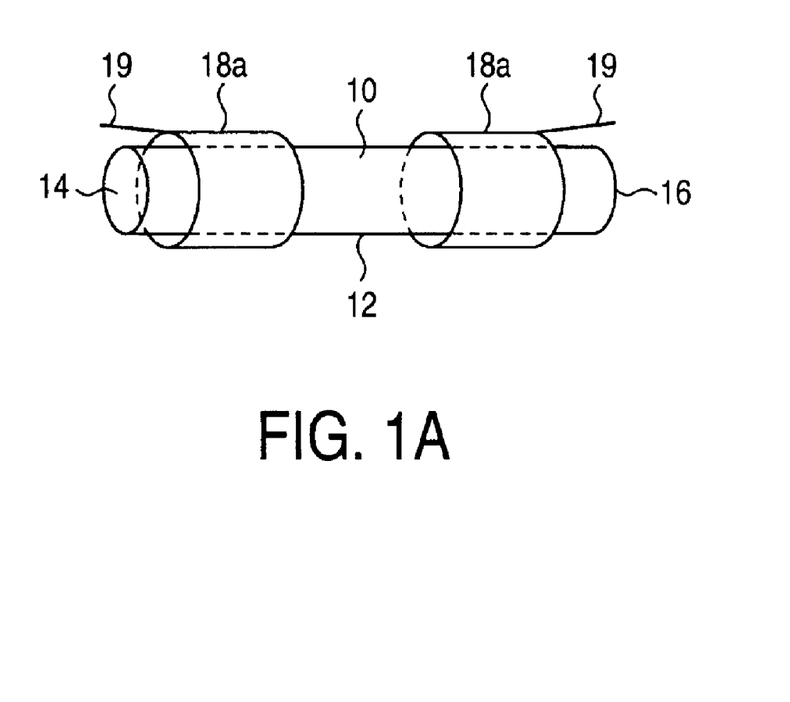
FIGS. 1A and 1B depict embodiments of the invention having a cylindrically-shaped chamber and contactless electrodes that are either cylindrically-shaped (FIG. 1A) or ring-shaped (FIG. 1B).
Figure 1B:
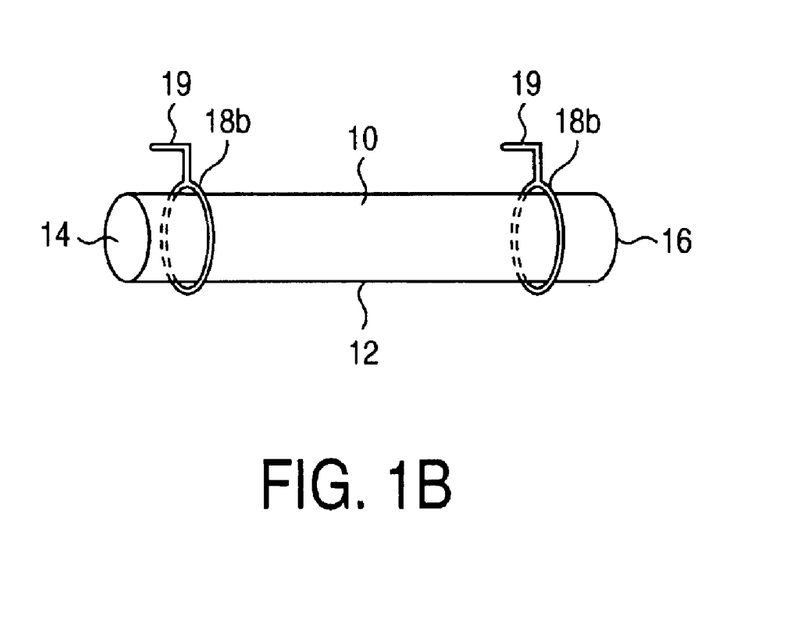

Referring now to the figures, FIG. 1A and 1B show a cylindrical chamber 10 defined by a chamber wall 12, the chamber having an inlet 14 and an outlet 16. The chamber wall 12 is in close proximity to electrodes 18. The electrodes shown in FIG. 1A are cylindrically shaped electrodes 18$a$; and the electrodes shown in FIG. 1B are ring shaped electrodes 18$b$, and the electrodes 18 are disposed at opposite ends of the chamber 10. Each electrode 18$a$, 18$b$ has a lead 19 providing electrical contact with external circuitry, such as a high frequency alternating potential source or control loop circuitry. The cylindrical chamber such as shown in FIGS. 1A and 1B may be a portion of tubing, for example, narrow-bore silica tubes such as are commonly used in capillary electrophoresis applications. The tube may be of any other suitable material, including materials suitable for the substrate (as discussed below). In one embodiment, the chamber wall is made of a material having suitable insulative properties, including both chemical and electrical insulative properties. Where the chamber wall is made of a material that lacks suitable insulative properties, such as chemical or electrical insulative properties, a separate layer of insulative material is included and may be disposed on the interior surface of the chamber wall (the surface defining the chamber) or may be disposed between the chamber wall and the electrode. The skilled practitioner will readily be able to determine suitability of materials for use in particular embodiments, given factors such as desired temperature range, composition and quantity of typical analyte solutions, range of operating conditions, etc. The skilled practitioner will also readily be able to determine chemical and/or electrical insulative properties of said materials as well as further materials known in the art which may be suitable for incorporation into particular embodiments. The distance from the interior surface of the chamber wall to the electrode may range from about 0.01 $\mu$m to about 10 millimeters. In certain embodiments, this distance may be in the range of about 0.05 $\mu$m to about 4 millimeters, and in some embodiments in the range of about 0.1 $\mu$m to about 2 millimeters. One of skill in the art will recognize that the design of the device will balance several factors, including (1) distance from the electrode to the fluid in the chamber, (2) frequency of applied potential, (3) peak-to-peak amplitude of the applied potential. A larger distance from the electrode to the fluid in the chamber will decrease the capacitive coupling, requiring greater electrical power. Also, parasitic coupling between the electrodes will rise to form a substantial loss. In certain embodiments the electrodes 18 are disposed directly against the chamber wall and the chamber wall has an electrical insulative property. In this way the contactless coupling of the electrodes 18 with the fluid in the chamber through the chamber wall 12 is the most efficient. However, the high frequency energy can pass air (any gas) or vacuum so the direct contact is not necessary and an arbitrary layer of air (or space) between the electrodes 18 and the chamber wall 12 can be present in some embodiments. Often, the relative capacitance of polymers is better than air, so it is typically advantageous to not have an air gap. The volume of the chamber can range from nanoliter in microdevices to such big volumes as tens of milliliters in preparative devices.

Figure 2:
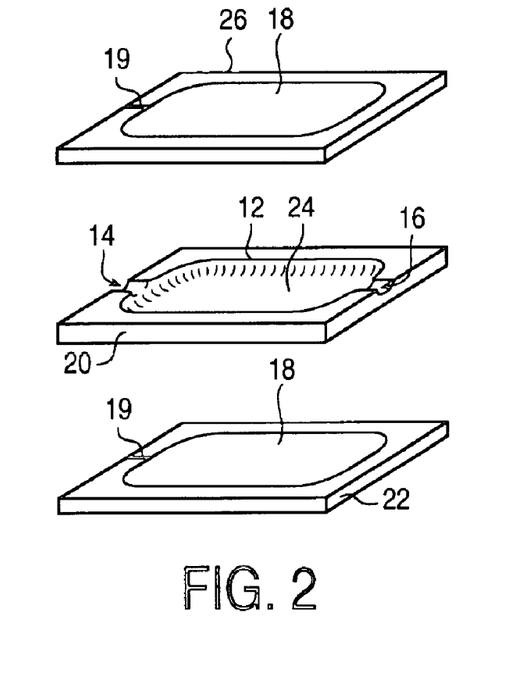
FIG. 2 shows a device according to the present invention that has separate layers stacked together.

In one embodiment, shown in FIG. 2, a planar substrate 20 defines a recess 24 such that the chamber 10 is formed by a cover plate 26 covering recess 24. The chamber wall 12 thus is a portion of the planar substrate 20 around the recess 24 and a portion of the cover plate 26 adjacent the recess 24. The planar substrate 20 with the cover plate 26 also defines an inlet 14 to the chamber 10 and an outlet 16 from the chamber 10. It should be understood that the Figures show only a portion of the device bearing the chamber 10, and that other components can be included as part of the device, such as fluid reservoirs, capillaries, analysis sites, vents, detection sites, interfaces to detectors, and/or waste ducts, each of which may be in fluid communication with the chamber 10. In FIG. 2, the planar substrate 20 bearing the chamber 10 is sandwiched between the cover plate 26 and the base plate 22, each bearing the electrodes 18, each electrode 18 having a lead 19 providing electrical contact to the electrode 18. In particular embodiments, at least a portion of the chamber 10 is disposed between the electrodes 18. In FIG. 2, the planar substrate 20, cover plate 26, and base plate 22 are all formed of a material having suitable chemical and electrical insulative properties; thus, when planar substrate 20, cover plate 26, and base plate 22 are all brought together, laminar fashion, or sandwich-like, a layer of insulative material is disposed between the chamber 10 and the electrodes 18. In another embodiment, one or more of the planar substrate 20, the cover plate 26, and the base plate 22 is formed of a material that lacks suitable insulative properties, necessitating the addition of a layer of insulative material between the electrodes 18 and the chamber 10. The layer of insulative material may be disposed on the interior surface of the chamber wall (the surface defining the chamber) or may be disposed between the wall and the electrode, e.g a membrane of insulative material disposed between the planar substrate 20 bearing the chamber 10 and at least one of the other planar substrates 22 bearing the electrodes 18. Examples of methods of depositing layers of materials includes vapor deposition of polymers, coating with Teflon®-AF, static coating procedures as used in the capillary electrophoresis arts (PEG, PAA, PVA), dielectric inks available from, e.g. Polyflex Circuits (Cranston, R.I.).

Figure 3:
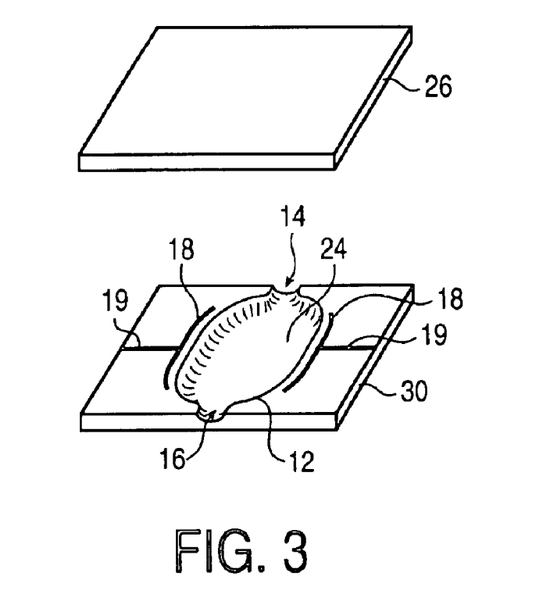
FIG. 3 shows a device according to the present invention having the chamber and electrodes on a single substrate.

FIG. 3 shows another embodiment wherein a single substrate 30 defines a recess 24, such that the chamber 10 is formed by a cover plate 26 covering recess 24. The chamber wall 12 thus is a portion of the substrate 30 around the recess 24 and a portion of the cover plate 26 adjacent the recess 24. The substrate 30 with the cover plate 26 also defines an inlet 14 to the chamber 10 and an outlet 16 from the chamber 10. The substrate 30 also bears two electrodes 18, one on either side of the recess 24, each electrode having a lead 19 providing electrical contact to the electrode 18.

Figure 4:
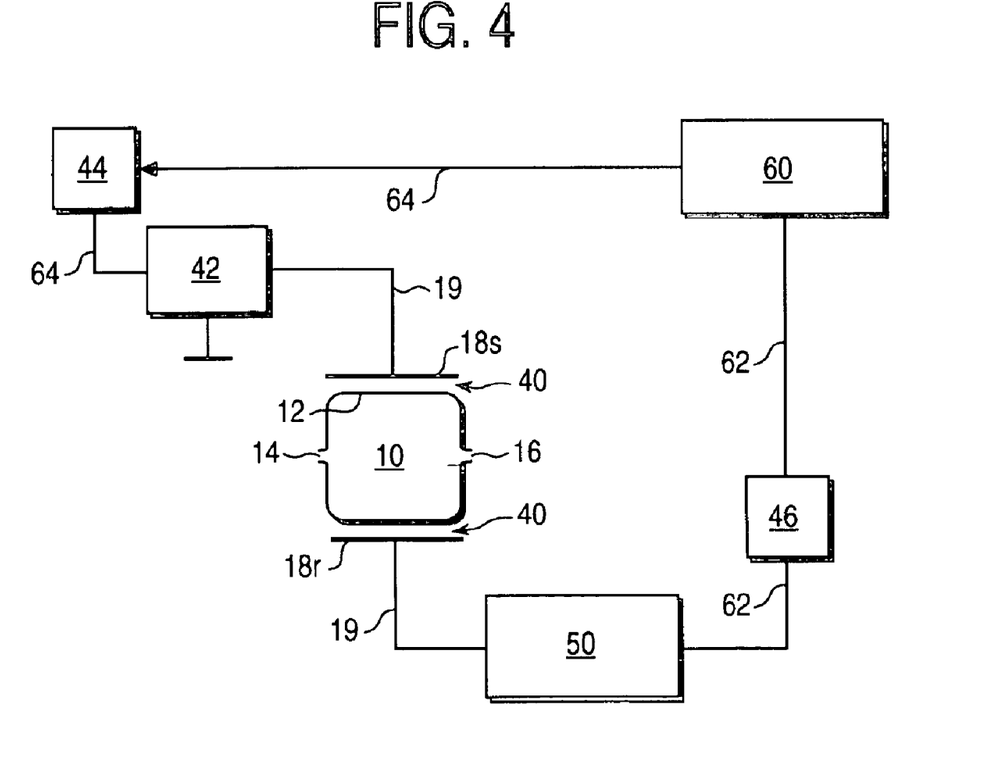
FIG. 4 schematically illustrates a device having a high-frequency alternating potential source capacitively coupled to a heated site comprising a chamber for holding a sample fluid.

FIG. 4 shows a setup for use of a chamber 10 in accordance with the present invention. The chamber has an inlet 14 and an outlet 16 allowing fluid to enter and exit the chamber 10, respectively. The chamber 10 is defined by a chamber wall 12, at least a portion of which is adjacent a layer of insulative material 40. Electrodes 18r, 18s are disposed closely adjacent the chamber 10 and separated from the chamber 10 by the layer of insulative material 40. In some embodiments, the chamber wall 12 may be formed of the insulative material 40, and in other embodiments, the chamber wall 12 is a distinct material from the insulative material 40. Each electrode 18r, 18s has a lead 19 providing electrical contact to the electrode 18r, 18s. One electrode 18s is in electrical communication with a high frequency potential source 42. The other electrode 18r is in electrical communication with control loop circuitry that includes, in the embodiment shown in FIG. 4, a receiver 50, a controller 60, and appropriate interfaces (control interface 44, receiver interface 46). The receiver 50 can comprise any suitable circuitry that receives the signal and processes the signal. In the example embodiment shown in FIG. 4, the receiver 50 has a circuit, which is able to evaluate a modified high frequency signal generated by a fluid in the chamber. The signal can typically be a high frequency current, which is dependent on conductivity and temperature of the fluid in the chamber.

The receiver 50 is interfaced to the controller 60 via a receiver interface 46 over control receiver lines 62. In one embodiment, the controller 60 comprises a programmable microprocessor, and the receiver interface 46 comprises an analogue to digital converter. The controller 60 is also interfaced to the high frequency potential source 42 via a control interface 44 over control source lines 64. In an embodiment, the control interface 44 comprises a digital to analogue converter. In certain other embodiments, one or both of the control interface 44 and receiver interface 46 may be omitted where the controller 60 may be directly in communication with the high frequency potential source 42 and/or the receiver 50. In one embodiment the controller 60 applies user supplied parameters (e.g. duration of heating, desired temperature, number of repeated heat/cool cycles) to perform the desired functions.

In operation, the high frequency potential source 42 supplies the electrode 18s with a high frequency signal. The high frequency signal is coupled to the other electrode 18r through the chamber 10. Fluid in the chamber 10 is heated as a result of this coupling, and the signal is modified as a function of at least one characteristic of the fluid. Electrode 18r receives the modified signal, which is related to the high frequency potential supplied by the high frequency potential source 42 and also is related to the at least one characteristic of the fluid. The receiver 50 processes the signal and passes the processed signal to a receiver interface 46. The controller 60 analyses the signal obtained via the receiver interface 46 and, based upon program parameters and user input, provides suitable control signals to the high frequency potential source 42 via the source interface 44. In one exemplary embodiment, the controller 60 provides for cyclical controlled heating of the fluid in the chamber, such as would be useful in performing PCR or a similar process. Conditions for performing PCR reactions are well known in the art and the skilled practitioner will be able to determine specific conditions of time and temperature to be applied to the fluid in the chamber, in embodiments where the chamber is a chamber for performing PCR reactions. Such conditions are taught in the literature, e.g. PCR by M. J. McPherson, S. G. Moller, Springer-Verlag (New York) July 2000.

The modified signal that is received at the electrode 18r is dependent on one or more characteristics of the fluid including temperature, conductivity, permittivity, and composition of the fluid. Composition of the fluid refers to solvents used and to concentrations of solutes, especially salts. By monitoring the modified signal the characteristics of the fluid can be monitored over time, and the high frequency potential source can be controlled to modifiy the amount of heating of the fluid. In a PCR reaction, the salt concentration shifts very slightly, and the solvent also remains essentially constant; permittivity also remains essentially constant over the course of a given PCR reaction. The variables having the strongest effect on the modified signal are thus the temperature and conductivity. This method of monitoring the temperature of the fluid measures the internal temperature of the fluid by direct measurement, as opposed to measuring the temperature of a material in contact with the fluid; also, the temperature measurement is done via contactless measurement.

The substrate should be stable over the conditions used for the heating of the fluid and may be any material suitable for forming liquid handling structures such as channels, reservoirs, capillaries, tubes or such like structures. Such liquid handling structures are referred to generically herein as "chambers". In certain embodiments, substrates known to be useful for manufacture of microfluidic structures are used. Some examples of such substrates are taught in co-owned patents issued to Kaltenbach et al., such as U.S. Pat. Nos. 5,658,413 and 6,093,362. In other embodiments, the substrate material is selected from any suitable polymer, ceramic, or silicaceous material (including glass). Polymer materials contemplated herein include materials selected from the following classes: polyimide, polycarbonate, polyester, polyamide, polyether, polyolefin, or mixtures thereof. In some embodiments, the substrate comprises a polyimide material such as those available under the trademarks Kapton® or Upilex® from DuPont (Wilmington, Del.). Depending on the intended application, either polymer materials or silicaceous materials (such as glass materials) may have more favorable properties. For example, polymer materials tend to have thermal qualities such that the polymer materials act as thermal insulators. In contrast, glass materials tend to behave more as heatsinks. In embodiments directed to providing a thermal cycler, the PCR reactions can be performed in chambers formed of either polymer or silicaceous materials (or both), however it's a nice feature to cycle faster (see also WO0060108-A1). The liquid handling structure may be formed by any suitable process known in the art, e.g. injection molding, buildup or stacking of laminar materials (stacked planar structures), etc.

The electrodes are any suitable electrically conducting material, such as metal or metal alloy, including copper, gold, aluminum, conductive polymers, conductive paints, conductive pastes, and conductive ink for screen painting is available from Poly-Flex Ltd (UK) or Acheson Colloiden (NL). The geometry of the electrodes, their shapes and their spatial relationship to each other and to the chamber, affect the efficiency of power transfer from the alternating potential at the electrode to the fluid in the chamber. Preferably, but not necessarily, the capacitance of the capacitive coupling should be less then the resistance of the heated fluid.

The capacitance of the coupling can be reduced or minimized in two ways: (i) decreasing the thickness of the wall and/or the insulative material, (ii) increasing the frequency of the alternating potential. At any rate, the designer of the specific embodiment should pay attention that the capacitive coupling of the electrodes to the fluid provides a sufficient transfer of energy to heat the fluid to a desired temperature. In the case of the cylindrical electrode configuration described in the examples section, below, the capacitive coupling is strong enough to transfer sufficient energy even at relatively low frequency of 20 MHz.

In one embodiment, one or more of the electrodes are inside the chamber (like filaments, ribbons, or 'fins' extending through or jutting into the chamber). In another embodiment, the electrodes are directly adjacent to or within the walls of the chamber (and the walls may be formed of or coated with insulative material); the electrodes surround the chamber (ring-shaped or cylindrical electrodes) in such an embodiment. In an exemplary embodiment, the chamber is the inside volume of a GC-capillary or a Kapton® polyimide tube and the electrodes are sleeves around, insulated by the chamber's wall.

The high frequency potential source may be any source of high frequency potential known in the art. The high frequency potential source may also be designed as a high frequency current source giving, however, a drop of high frequency potential at the electrodes. The maximum amplitude of the high frequency potential as measured between the two electrodes may range from at least about 0.01 V up to about 2000 V. In some embodiments said amplitude may range from at least about 0.1 V up to about 500 V. In other embodiments said amplitude may range from at least about 2 V up to about 400 V The frequency of the alternating high frequency potential is between about 100 Hz and about 700 MHz, preferably between about 1000 Hz and about 500 MHz, more preferably between about 10 kHz and about 100 MHz, most preferably between about 50 kHz and about 50 MHz. Without being limiting of the invention as delineated in the claims, it is believed the mechanism of heating of the fluid is due to ions in the fluid moving back and forth under influence of the applied high frequency potential. This movement of the ions among the other molecules in solution gives rise to frictional heating of the solution (on a molecular level within the solution). Energy from the high frequency potential source is coupled to the fluid, heating the fluid directly (direct heating). This can be contrasted to methods that heat the fluid by heating a substance in contact with the fluid, thus heating the fluid by conduction from the substance heated (indirect heating). Direct heating generally results in more even heating throughout the fluid, avoiding temperature gradients in the fluid that may be undesirable.

An insulative material is disposed between the electrode and the chamber so that the electrode does not contact a fluid present in the chamber (i.e. the electrodes are contactless). The insulative material has a high resistance to the flow of direct electrical current and also prevents chemical contamination of the fluid in the chamber—that is to say, the insulative material is both electrically and chemically insulative. The insulative material may comprise layers of separate materials, for example a first electrically insulative layer directly contacting the electrode and a second chemically insulative layer isolating the electrode and first layer from the fluid in the chamber. The electrically insulative property substantially prevents electrode chemical reactions and surface processes like sorption from occurring normally at the boundary between electrically conductive electrodes and the fluid in the chamber as a consequence of the pass of electric current. The chemically insulative property substantially prevents contamination of the fluid by undesirable materials in the electrode or first electrically insulative layer. The insulative material may be any suitable material or combination of materials providing the desired insulative properties, including glass, polymers such polyimide or PEEK. Suitable materials should exhibit sufficiently high electrical resistance, chemical inertness, ability to pass the high frequency potential signal (allowing the fluid to couple the signal), and strength to withstand the operating conditions of the device. In one embodiment, the electrode may be buried in the substrate that defines the chamber, such that the substrate is used as part or all of the insulative material. In certain embodiments, the thickness of the insulative material may range from at least about 10 micrometers up to about 1000 micrometers. In certain other embodiments, the thickness of the insulative material may range from at least about 0.1 micrometers up to about 10 millimeters.

The control loop circuitry is used to measure a modified signal related to the alternating high frequency potential, such as the current flowing to the electrodes, the potential between the electrodes, the phase relation between voltage and current as the alternating potential is applied to the electrodes. The modified signal may be correlated to the temperature and/or the conductance of the fluid to allow determination of the temperature and/or conductance of the fluid. The process of establishing the correlation is described below.

One embodiment of the present invention provides for a thermal cycler useful for performing PCR reactions on small samples (generally between about 0.01 microliters and about 1 milliliter, preferably between about 0.1 microliters and about 500 microliters, more preferably between about 1 microliter and about 200 microliters; the chamber is designed to have the desired capacity for holding fluid containing the PCR reaction mixture). Such a thermal cycler can also be used for reactions other than PCR that require thermal cycling or other thermal control. In this embodiment, the control loop is adapted to control the thermal cycling necessary for the PCR reaction. Reaction solutions and conditions may be determined by one of skill in the art given prior art disclosures relating to PCR reaction solutions and conditions. Reactions similar to PCR which utilize a thermal cycle include ligase chain reaction, linear amplification, and others known in the art. It will be readily apparent that still other reactions which require controlled heating for a period of time may be performed in chambers according to the present invention, and that such chambers as may be made without undue experimentation are within the scope contemplated by the current disclosure.

EXAMPLES

The practice of the present invention will employ, unless otherwise indicated, conventional techniques of device manufacture, material molding and shaping, applying coatings, synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

Figure 5:
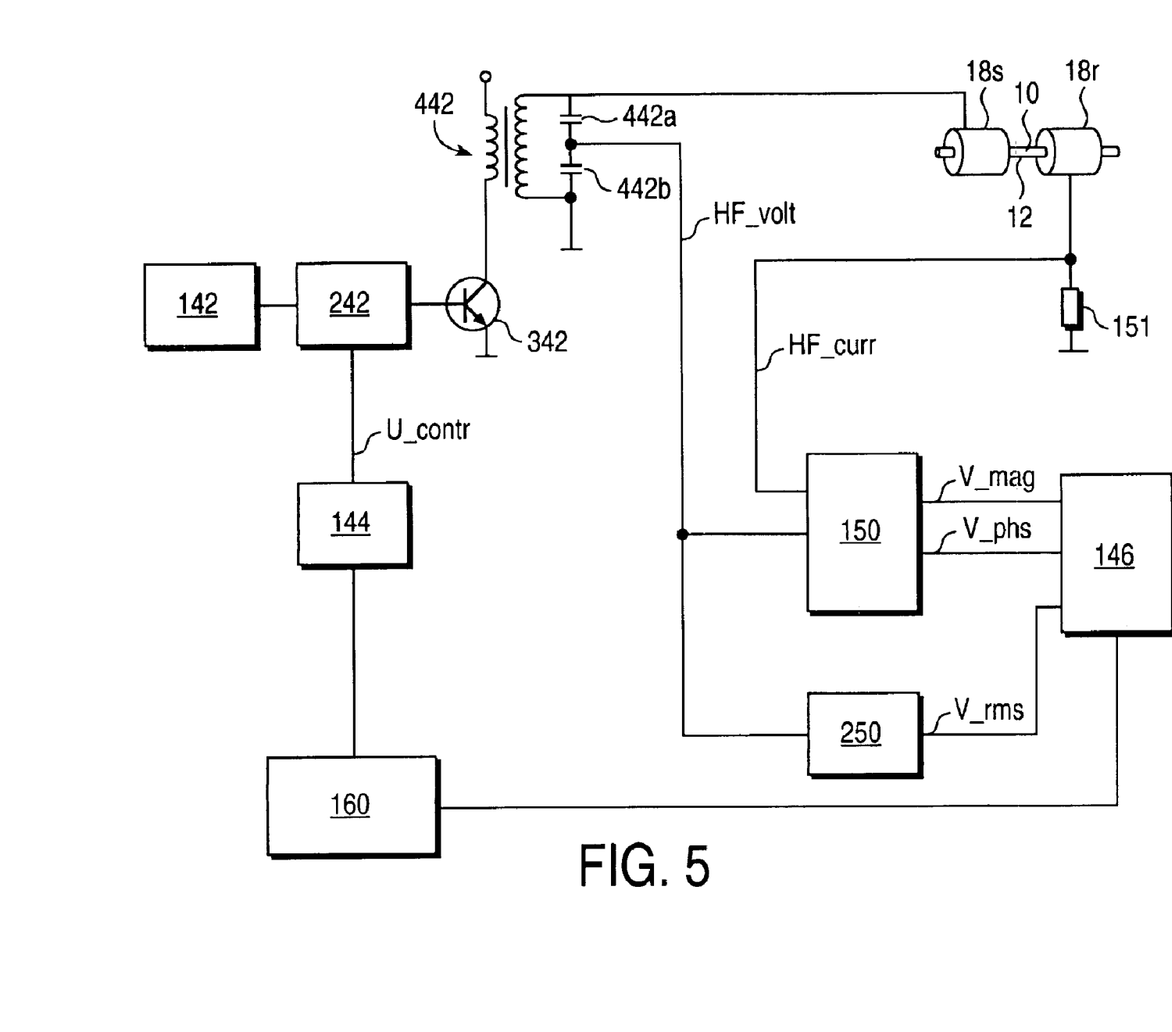
FIG. 5 schematically illustrates an exemplary embodiment according to the current invention.

An embodiment according to the current invention is shown in FIG. 5. A chamber 10 is defined by a chamber wall 12 composed of polyimide, which serves as a chemically and electrically insulative material between the electrodes 18r, 18s and the chamber 10. The chamber 10 and the electrodes 18s, 18r have a cylindrical geometry. The chamber 10 is a tube having an inner diameter of 600 micrometers and an outer diameter of 720 micrometers. The electrodes 18s, 18r are about 10 millimeters long and fit tightly around the outer diameter of the tube, with no air gap between the tube and the electrodes. A length of tube about 7 millimeters long lies between the electrodes 18s, 18r, thus the volume of the chamber between the two electrodes 18s, 18r is about 2 microliters.

One electrode 18s (the electrode on the left in the figure) is the source electrode (or transmitting electrode) and is in electrical communication with a high frequency potential source. In this example, the high frequency potential source includes an oscillator 142 electrically connected to a controlled attenuator 242 that is itself connected to an amplifier 342. The amplifier 342 is electrically connected to a tuned transformer 442 that is connected to the electrode 18s.

The other electrode 18r (the electrode on the right in the figure) is the receiving electrode and is connected to the ground via a sensing resistor 151 with small resistance (of 10 Ohms). The receiving electrode 18r is in electrical communication with control loop circuitry including a gain and phase detector 150. The gain and phase detector 150 is interfaced with a controller 160 via an analogue-to-digital (A/D) converter 146. A power detector 250 is also interfaced with the controller 160 via the A/D converter 146. Both the gain and phase detector 150 and the power detector 250 are electrically connected to receive a reference signal from the tuned transformer 442 as described below. The controller 160 is interfaced to the controlled attenuator 242 via a digital-to-analogue (D/A) converter 144.

In use, the oscillator 142 produces a signal with frequency of 20 MHz. The signal is led through the controlled attenuator 242, amplified by the amplifier 342 and transformed by the tuned transformer 442 to a maximum level of about 150 $V_{eff}$. This high frequency alternating potential is led to the chamber 10 where it is used for high frequency heating of fluid within the chamber 10. The controlled attenuator 242, the attenuation of which is controlled by means of the signal U_contr via the digital-to-analogue (D/A) converter 144, allows the control of the high frequency alternating potential at any desired value in the range zero to about 150 Veff. The capacitance of the tuned transformer 442 includes two capacitors (442a, 442b) that provide for dividing the high frequency alternating potential by a factor of about 100 to obtain in this way a reference signal of about 0–1.5 $V_{eff}$, which is proportional to the high frequency alternating potential and which serves as information about the high frequency alternating potential for other circuitry. This high frequency signal is denoted HF_volt.

In this embodiment the high frequency alternating potential is coupled contactlessly via the chamber wall 12 to the electrolyte solution (the fluid) inside the chamber. As shown in FIG. 5, the left electrode 18s is the transmitting (or source) electrode and is supplied with the high frequency alternating potential. The high frequency alternating potential from the transmitting electrode supplies the high frequency current that passes by means of capacitive coupling through the chamber wall into the electrolyte solution inside, then passes through the electrolyte solution (the fluid) in the chamber and a modified signal is received by the receiving electrode 18r (the electrode on the right). The portion of the chamber 10 positioned between the electrodes 18s, 18r is where the fluid is most actively heated by Joule heating due to the passing high frequency current.

The drop of high frequency voltage at the sensing resistor 151 is proportional to the high frequency current passing through the fluid. This high frequency signal is denoted HF_curr. The gain and phase detector 150 processes both high frequency signals, HF_volt and HF_curr, and provides two DC signals: V_mag and V_phs. The V_mag signal is given by $V\_mag = Const*log(HF\_curr/HF\_volt)$, where log is the natural logarithm and Const is a certain constant, which is a characteristic of the particular arrangement. The V_phs signal is proportional to the phase shift between HF_curr and HF_volt.

The power detector 250 determines the total power input and generates the DC signal denoted as V_rms, which is proportional to HF_volt.

Each of the DC signals V_mag, V_phs and V_rms are digitalized by the analogue-to-digital (A/D) converter 146 and read by the controller 160, which comprises a computer with suitable software for controlling heating of the fluid. Principle of Measurement and Control of the Temperature Measurement of Temperature The computer software allows processing of the DC signals, V_mag, V_phs and V_rms, and also provides for obtaining information about parameters of the fluid in the chamber 10.

The conductivity of the fluid in the chamber, which can be a solution of electrolytes, is given by Kappa=HF_curr/HF_volt, so Kappa can be obtained as Kappa=exp(V_mag/Const). The value of Const can be easily obtained by calibrating by means of a fluids with known conductivities.

The conductivity of a solution is basically dependent on two quantities: (i) on the concentration of solutes, particularly ionic solutes, present in the solution, (ii) on the temperature of the solution. Both concentration and temperature dependencies can be independently determined by means of a calibration procedure for any solution and described as a Mathematical function of two variables: concentration and time.

Inverse application of the Mathematical function (determined through calibration) allows the determination of both the concentration of the solution and the temperature of the solution. The computer software can proceed as follows:

1. At the beginning the controlled attenuator 242 is set by software to a maximum attenuation, so there is no heating voltage and the solution in the chamber has a certain known ambient temperature Tamb.
2. At time Tstart the computer software now sets a certain value U_contr by means of the D/A converter 144. This brings a certain level of heating voltage at the chamber. At a very short time after Tstart the software reads the value of Kappa_start. At the short time after Tstart the temperature is virtually the same as at Tstart due to a certain heat inertia of the system. As the temperature is still Tamb, the value Kappa_start gives the information on the concentration of the solution when the Mathematical function is inversely used. In this way the concentration of the solution is determined.
3. When a conductivity Kappa is now measured in any time, also the temperature can be determined as the concentration of the solution can be calculated when the Mathematical function is inversely used. In this way the temperature of the solution is determined. As noted previously, in an embodiment where the apparatus is designed for use as a thermal cycler for use in running PCR reactions, the reactions typically may be conducted under conditions of sufficiently high buffer and salt concentration that the concentration term remains essentially unchanged or changes in a predictable manner over the course of the reaction.

Figure 6:
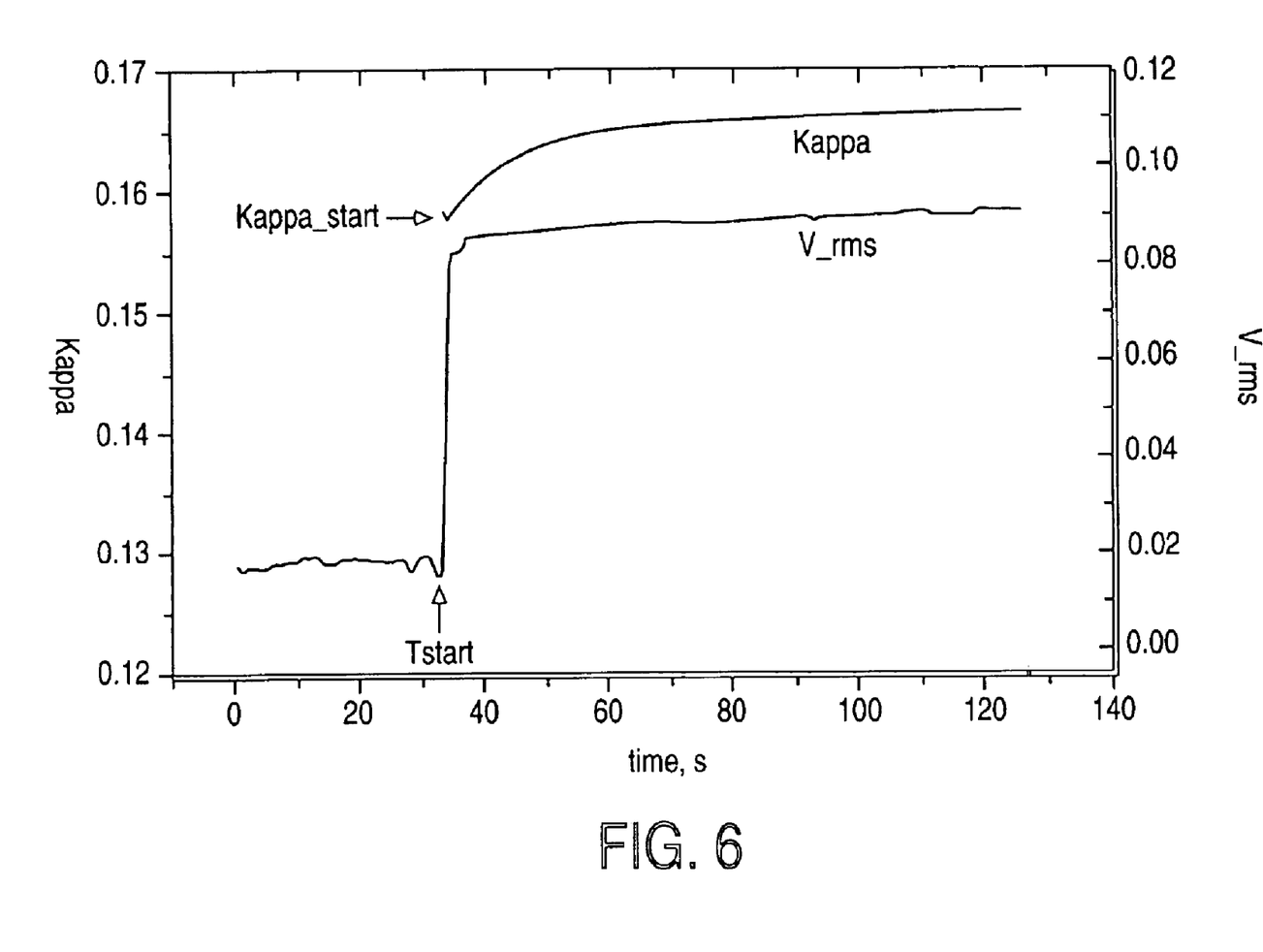
FIG. 6 gives experimental data indicating the change in conductivity of the fluid over time as the applied potential is increased.

As shown above, the signal V_mag is essential for determining temperature of the solution. Other two signals, V_phs and V_rms, can however serve for obtaining additional information about the system and possible corrections in calculations. To demonstrate a behavior of the real system, enclosed FIG. 6 shows a response of Kappa to a certain jump in the high frequency alternating potential.

Control of Temperature

The previous example has shown how temperature can be determined when a certain value of the U_contr signal is applied. The process can be, however, reversed and the computer program can serve for the control of the temperature to a desired value T_desir by means of U_contr signal. The computer software can proceed as follows:

1. and 2. These are the same as in the previous example. As a result, the concentration of the solution is determined.

3. When the concentration is known, the conductivity Kappa_desir corresponding to desired temperature T_desir is calculated by means of the Mathematical function. When a conductivity Kappa is now measured in any time, the difference between the desired and real conductivity, Kapa_desir−Kappa, can be calculated. This difference is used to correct value of the U_contr signal to get this difference zero, Kapa_desir _Kappa= 0, by means of the computer feedback control. This way the desired temperature T_desir of the solution can be reached.

Use as a Flow Sensor

Figure 7:
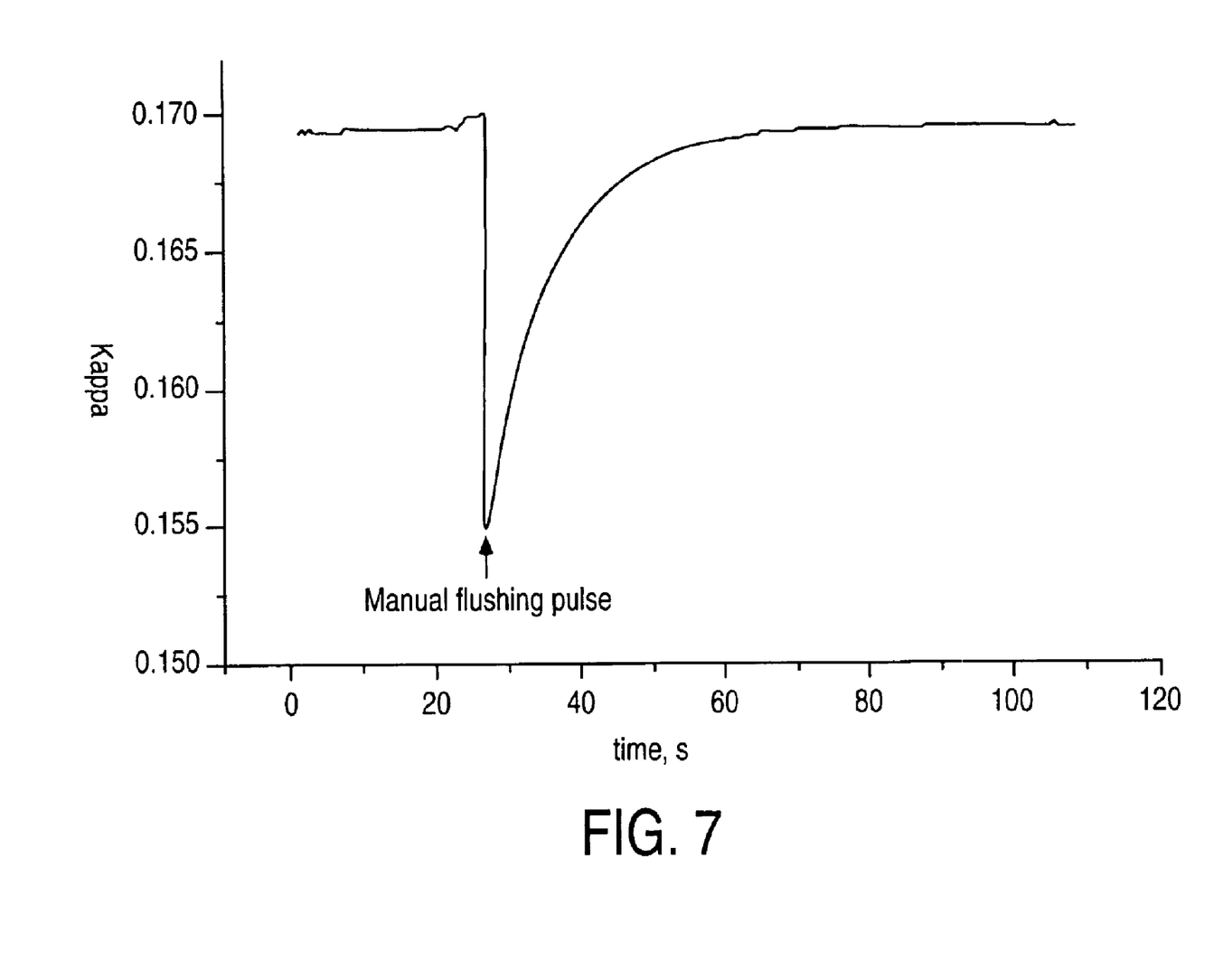
FIG. 7 shows a response of the conductivity Kappa on the flushing pulse manually reached by a syringe.

The temperature that can be reached in the active part of the chamber depends also on the velocity of the flow in the chamber. The equipment can therefore also be used for a determination of the velocity of the flow. To document this, FIG. 7 shows a response of the conductivity Kappa on the flushing pulse manually reached by a syringe.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A device for using an alternating potential source to heat a fluid while determining a characteristic of the fluid, the device comprising:

a substrate having a chamber disposed therein for holding the fluid;

at least two electrodes, each electrode coupled to the chamber via a contactless coupling, said alternating potential source providing a high frequency potential between the electrodes to heat the fluid; and a receiver for receiving a signal, the receiver electrically coupled to at least one electrode, wherein the signal is used to determine the characteristic of the fluid and to provide feedback to control the alternating potential source.

2. The device according to claim 1, wherein the device is adapted to coupling energy from the high frequency potential to the fluid in the chamber, wherein the high frequency potential has a frequency of at least about 100 Hz up to a maximum of about 700 MHz.

3. The device according to claim 1, wherein the characteristic of the fluid is selected from conductance and temperature.

4. The device according to claim 1, wherein each electrode is separated from the chamber by a layer of insulative material.

5. The device according to claim 4, wherein the layer of insulative material is at least about 0.1 micrometer thick and is less than about 10 millimeters thick.

6. The device according to claim 4, wherein the layer of insulative material comprises a polymeric material.

7. The device according to claim 4, wherein the layer of insulative material comprises a portion of the substrate.

8. The device according to claim 4, wherein the layer of insulative material is both chemically insulative and electrically insulative.

9. The device according to claim 1 wherein the chamber is adapted to hold a volume of fluid of about 1 nanoliter to about 10 milliliters.

10. The device according to claim 1, wherein the substrate comprises a first planar structure having a recess and a second planar structure adapted to fit over the recess to form the chamber.

11. The device according to claim 1, wherein the substrate comprises at least two planar structures disposed adjacent each other, the electrodes disposed upon at least one of the planar structures, at least a portion of the chamber disposed between at least two of the electrodes.

12. The device according to claim 1, wherein the chamber is cylindrically shaped and has two opposing ends, wherein the electrodes are cylindrically shaped and are disposed concentrically around the chamber, one electrode at each opposing end.

13. The device according to claim 1, wherein the chamber is cylindrically shaped and has two opposing ends, wherein the electrodes are ring shaped and are disposed concentrically around the chamber, one electrode at each opposing end.

14. The device according to claim 1 further comprising the alternating potential source.

15. The device according to claim 14, further comprising a controller operably coupled to the alternating potential source, said controller controlling the alternating potential to heat the fluid in repeated cycles.

16. The device according to claim 1, further comprising a controller adapted to controlling the alternating potential source, the controller in electrical communication with the receiver.

17. The device according to claim 16, wherein the controller comprises a microprocessor.

18. The device according to claim 17, wherein the microprocessor is programmed to deliver repeated cycles of heating and cooling to the fluid in the chamber.

19. The device according to claim 17, wherein the microprocessor is programmed to deliver a defined period of heating to the fluid in the chamber.

20. The device according to claim 16, wherein the device is a thermal cycler.

21. A method of heating a fluid and determining a characteristic of the fluid, the method comprising:

placing the fluid in a chamber, said chamber adjacent two electrodes, each electrode coupled to the chamber via a contactless coupling;

applying a high frequency potential to at least one electrode, said high frequency potential being coupled to the fluid to result in heating of the fluid;

receiving a modified signal related to the high frequency potential; and monitoring the modified signal to determine the characteristic of the fluid and to control the high frequency potential wherein the characteristic of the fluid is selected from conductivitiy and temperature.

22. The method according to claim 21, wherein the high frequency potential has a frequency of at least about 100 Hz up to a maximum of about 700 MHz.

23. The method of claim 21, further comprising heating the fluid in multiple repeated cycles.

24. A device for heating a fluid and measuring a characteristic of said fluid, the device comprising:

a substrate having a chamber disposed therein;

at least two electrodes coupled to the chamber;

an insulative material disposed between each electrode and the chamber and separating each electrode from the chamber;

means for providing a high frequency potential between the electrodes; and a control loop electrically coupled to at least one electrode to control the extent of heating of the fluid, said control loop measuring a signal related to the high frequency potential wherein the signal is used to measure the characteristic of the fluid.

25. The device according to claim 24, wherein the device is adapted to coupling energy from the high frequency potential to the fluid in the chamber, wherein the high frequency potential has a frequency of at least about bout 100 Hz up to a maximum of about 700 MHz.

26. The device according to claim 24, wherein the characteristic of the fluid is selected from conductance and temperature.

27. A method of heating a fluid while measuring a characteristic of the fluid selected, the method comprising:

placing the fluid in a chamber having at least two electrodes coupled to the chamber, wherein an insulative material is disposed between each electrode and the chamber, said insulative material separating each electrode from the chamber;

providing a high frequency potential between the electrodes to result in heating of the fluid;

using circuitry connected to at least one electrode to measure a signal related to the high frequency potential;

determining the characteristic of the fluid using the signal; and using the signal to control the amount of heating of the fluid wherein the characteristic of the fluid is selected from conductance and temperature.

* * * * *